US010415014B2

(12) United States Patent
Ma et al.

(10) Patent No.: US 10,415,014 B2
(45) Date of Patent: Sep. 17, 2019

(54) METHOD FOR THE EX VIVO CULTIVATION OF ORAL MUCOSAL EPITHELIAL PROGENITOR CELLS AND ORAL MUCOSAL EPITHELIAL CELLS

(71) Applicant: Chang Gung Memorial Hospital, Linkou, Taoyuan (TW)

(72) Inventors: Hui-Kang Ma, Taoyuan (TW); Shih-Chieh Ma, Taoyuan (TW)

(73) Assignee: Chang Gung Memorial Hospital, Linkou, Taoyuan (TW)

( * ) Notice: Subject to any disclaimer, the term of this patent is extended or adjusted under 35 U.S.C. 154(b) by 103 days.

(21) Appl. No.: 15/454,876

(22) Filed: Mar. 9, 2017

(65) Prior Publication Data

US 2017/0260505 A1 Sep. 14, 2017

Related U.S. Application Data

(60) Provisional application No. 62/306,936, filed on Mar. 11, 2016.

(51) Int. Cl.
*C12N 5/071* (2010.01)

(52) U.S. Cl.
CPC ........ *C12N 5/0632* (2013.01); *C12N 2500/84* (2013.01); *C12N 2500/90* (2013.01); *C12N 2501/11* (2013.01); *C12N 2501/33* (2013.01); *C12N 2501/999* (2013.01); *C12N 2502/03* (2013.01); *C12N 2509/00* (2013.01)

(58) Field of Classification Search
CPC .............. C12N 5/0632; C12N 2500/84; C12N 2500/90; C12N 2501/11; C12N 2501/33; C12N 2501/999; C12N 2502/03; C12N 2509/00
USPC .......................................................... 435/381
See application file for complete search history.

(56) References Cited

PUBLICATIONS

Utheim et al., Culture of Oral Mucosal Epithelial Cells for the Purpose of Treating Limbal Stem Cell Deficiency, Journal of Functional Biomaterials, 7, 6, (Mar. 1, 2016), pp. 1-18.*

Chen et al., A New Isolation Method of Human Limbal Progenitor Cells by Maintaining Close Associating with Their Niche Cells, Tissue Engineering: Part C, vol. 17, No. 5 (2011), pp. 537-548.*

Johansson et al., Platelet lysate: a replacement for fetal bovine serum in animal cell culture?, Cytotechnology, 42 (2003), pp. 67-74.*

Lim et al., Lentiviral Vector Mediated Thymidine Kinase Expression in Pluripotent Stem Cells Enables Removal of Tumorigenic Cells, PLoS One, vol. 8, Iss. 7, (Jul. 2013), pp. 1-16.*

Mill Creek Life Sciences, PLTMax®, The Research Behind the Results, Available Online at: www.millcreekls.com/research-behind-results, at least as early as Sep. 21, 2015 per Internet Archive Wayback Machine.*

Lekhanont et al., A serum- and feeder-free technique of culturing human corneal epithelial stem cells on amniotic membrane, Molecular Vision, 15 (2009), pp. 1294-1302.*

Cascade Biologics, Supplement S7, Defined, Animal Origin-Free Supplement for Human Keratinocyte Culutre, (Aug. 20, 2009), Available Online at: assets.thermofisher.com/TFS-Assets/LSG/manuals/Supplement_S7.pdf.*

Ilmarinen et al., Towards a defined, serum- and feeder-free culture of stratified human oral mucosal epithelium for ocular surface reconstruction, Acta Ophthalmologica, 2013, 91: pp. 744-750.*

CellnTEC, CnT-30 Datasheet, Accessed May 12, 2019, Available Online at: cellntec.com/products/cnt-30/#datasheet.*

CellnTEC, CnT-24 Datasheet, Accessed May 12, 2019, Available Online at: cellntec.com/wp-content/uploads/pdf/CnT-24.pdf.*

* cited by examiner

*Primary Examiner* — Jennifer M. H. Tichy
(74) *Attorney, Agent, or Firm* — Lewis Roca Rothgerber Christie LLP

(57) ABSTRACT

A method for the ex vivo cultivation of oral mucosal epithelial progenitor cells and oral mucosal epithelial cells includes: subjecting an oral mucosal tissue to an enzymatic digestion treatment with collagenase, so as to obtain cell aggregates which include oral mucosal epithelial progenitor cells and oral mucosal epithelial cells; cultivating the cell aggregates with an amniotic membrane in a serum-free platelet lysate-containing medium in the absence of feeder cells, so that the cell aggregates are adhered onto the amniotic membrane; and subsequently cultivating the cell aggregates adhered on the amniotic membrane in a serum-free proliferation-facilitating medium in the absence of feeder cells.

18 Claims, 4 Drawing Sheets

METHOD FOR THE EX VIVO CULTIVATION OF ORAL MUCOSAL EPITHELIAL PROGENITOR CELLS AND ORAL MUCOSAL EPITHELIAL CELLS

CROSS-REFERENCE TO RELATED APPLICATION

This application claims priority of U.S. Provisional Application No. 62/306,936, filed on Mar. 11, 2016.

FIELD

The disclosure relates to a method for the ex vivo cultivation of mucosal epithelial cells and mucosal epithelial progenitor cells, and more particularly to a method for the ex vivo cultivation of mucosal epithelial cells and mucosal epithelial progenitor cells in a serum-free and feeder-free condition.

BACKGROUND

The cornea, which allows light transmission to the retina, is important for normal vision. Particularly, the corneal epithelium plays an essential role in preserving normal vision by maintaining the avascularity and transparency of the cornea, and thus, it is important that proper functioning of the corneal epithelium be maintained. Renewal and repair of the corneal epithelium are mediated by corneal epithelial stem cells located mainly in the limbus, the narrow region between the cornea and the bulbar conjunctiva. Damage or depletion of the corneal epithelial stem cells, known as limbal stem cell deficiency (LSCD), gives rise to conjunctival invasion, which causes vascularization of the cornea with an associated profound loss of vision. Occurrence of LSCD might result from external factors and disorders (for example, thermal or chemical injuries, microbial infections, surgeries involving the limbus, Stevens-Johnson syndrome, ocular cicatricial pemphigoid, aniridia, etc.).

Cell transplantation has been considered as a promising approach to reconstruct the corneal epithelium of patients with LSCD. For instance, researchers have attempted to use oral mucosal epithelial cells (OMECs), embryonic stem cells, conjunctival epithelial cells, epidermal stem cells, dental pulp stem cells, bone marrow-derived mesenchymal stem cells, hair follicle bulge-derived stem cells, umbilical cord lining stem cells, and orbital fat-derived stem cells for treating LSCD. Among the aforesaid therapeutic non-limbal cell types, conjunctival epithelial cells and OMECs are the only laboratory cultivated cell sources which have been explored in humans.

Both of the corneal and oral mucosal epithelia are stratified, with tight junction proteins (such as connexin 43 (Cx43)) in the suprabasal layer and hemidesmosome proteins (such as integrins) in the basal layer. Moreover, keratin 3/76 is expressed in both the corneal and oral mucosal epithelia. Due to the resemblance of the oral mucosal epithelia to the corneal epithelia, as well as the easy availability of the oral mucosal epithelium (i.e. no invasive surgery is required to harvest the oral mucosal epithelium), cultivated oral mucosal epithelial transplantation (COMET) has been widely used to repair damaged corneal surfaces and as an important bridge therapy for acute or chronic corneal burns. Recently, the COMET procedure has also been applied to repair intraoral mucosal defects and esophageal mucosa during endoscopic mucosal resection procedures, suggesting that such procedure has the potential for a wide variety of clinical applications.

Nakamura et al. and Nishida et al. reported the original protocol for the ex vivo cultivation of OMECs for COMET in 2004 (see Nakamura et al. (2004), *Br. J. Ophthalmol.* 88:1280-1284; and Nishida et al. (2004), *N. Engl. J. Med.* 351:1187-1196). Specifically, the original protocol uses dispase II/trypsin to isolate OMECs from tissues and to disrupt the epithelium. To cultivate the isolated OMECs ex vivo, fetal bovine serum (FBS) and 3T3 mouse fibroblasts (serving as feeder cells) are deemed necessary in the original protocol since they facilitate cell adhesion and proliferation which in turn lead to formation of a confluent epithelial cell sheet. Furthermore, researchers have verified the potency of COMET for promoting wound healing in severe ocular surface burns and demonstrated the long-term persistence of OMECs in the transplanted corneas.

However, FBS and mouse-derived 3T3 feeder cells are xenobiotic materials which might give rise to transmission of zoonotic infections or unknown pathogens. When it particularly comes to the ex vivo cell expansion for clinical application, the use of xenobiotic materials, such as animal-derived serums and feeders, might increase the risk of transmission of diseases (e.g. bovine spongiform encephalitis). Therefore, an animal-derived component-free (ADCF) culture procedure, in particular a serum-free and feeder-free culture procedure, is in demand for the next generation of COMET.

SUMMARY

Therefore, an object of the present disclosure is to provide a method for the ex vivo cultivation of oral mucosal epithelial progenitor cells and oral mucosal epithelial cells that can alleviate at least one of the drawbacks of the prior art.

According to the disclosure, the method for the ex vivo cultivation of oral mucosal epithelial progenitor cells and oral mucosal epithelial cells includes:

- subjecting an oral mucosal tissue to an enzymatic digestion treatment with collagenase, so as to obtain cell aggregates which include oral mucosal epithelial progenitor cells and oral mucosal epithelial cells;
- cultivating the cell aggregates with an amniotic membrane in a serum-free platelet lysate-containing medium in the absence of feeder cells, so that the cell aggregates are adhered onto the amniotic membrane; and
- cultivating the cell aggregates adhered on the amniotic membrane in a serum-free proliferation facilitating medium in the absence of feeder cells, so that the oral mucosal epithelial progenitor cells and the oral mucosal epithelial cells in the cell aggregates proliferate.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
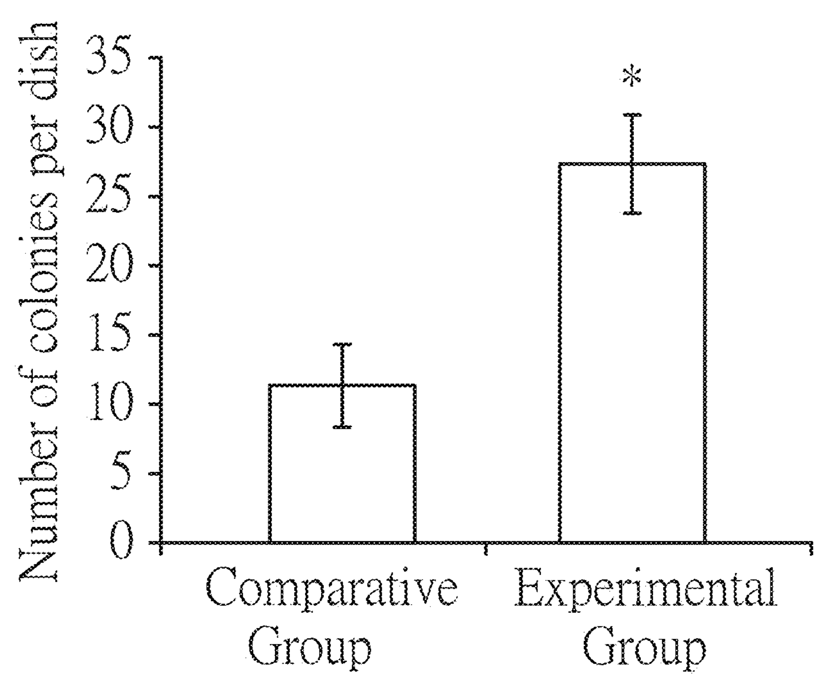
FIG. 1 illustrates the results of the colony formation assay with a bar chart of the number of colonies per dish for human oral mucosal epithelial cells and oral mucosal epithelial progenitor cells of Experimental and Comparative Groups.

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In order to avoid xenogenic infection from animal-derived components (such as FBS and 3T3 fibroblasts) used for the conventional COMET procedure, the applicants developed a novel animal-derived component-free (ADCF) culture procedure for generating mucosal epithelial sheets containing oral mucosal epithelial progenitor cells and oral mucosal epithelial cells (OMECs), where collagenase is used to replace conventionally used dispase II/trypsin-EDTA for digesting oral mucosal tissues with high-speed vortexing being involved, human platelet-derived product (such as PLTMax®) is used to replace conventionally used fetal bovine serum in supplemented hormonal epithelial medium (SHEM) for avoiding xenogeneic infection from animal-derived components, and a serum-free proliferation facilitating medium (such as EpiLife® medium) is subsequently used to eliminate contamination by submucosal mesenchymal cells.

Through the procedure mentioned above, the applicants found that OMECs cultivated in this manner are superior to OMECs cultivated according to the procedure of the prior art in generating human oral mucosal epithelial sheet with increased proliferative potential.

Accordingly, the present disclosure provides a method for the ex vivo cultivation of oral mucosal epithelial progenitor cells and oral mucosal epithelial cells, including:

subjecting an oral mucosal tissue to an enzymatic digestion treatment with collagenase, so as to obtain cell aggregates which include oral mucosal epithelial progenitor cells and oral mucosal epithelial cells;

cultivating the cell aggregates with an amniotic membrane in a serum-free platelet lysate-containing medium in the absence of feeder cells, so that the cell aggregates are adhered onto the amniotic membrane; and cultivating the cell aggregates adhered on the amniotic membrane in a serum-free proliferation facilitating medium in the absence of feeder cells, so that the oral mucosal epithelial progenitor cells and the oral mucosal epithelial cells in the cell aggregates proliferate.

As used herein, the term "ex vivo" refers to experimentation or measurements performed in or on living tissues in an artificial environment outside the host with the minimum alteration of the natural conditions.

The terms "cultivate" and "cultivating" as used herein, refer to the sustaining, propagating, growing and/or differentiating of cells outside of tissue or the body, for example in a sterile cell culture dish or flask. Moreover, the term "cultivation" as used herein, refers to the utilization of a culture medium as a source of nutrients, hormones and/or other factors helpful to propagate and/or sustain cells.

As used herein, "oral mucosal epithelial cells" refers to epithelial cells of the oral mucosa. The oral mucosa may be any mucosal surface or oral mucosal tissue found in the oral cavity, including but not limited to lingual surfaces, i.e., the surface membranes of the tongue; sublingual surfaces, i.e., the mucosal membranes lining the floor of the mouth; buccal surfaces, i.e., the mucosal membranes lining the cheeks; palatal surfaces, i.e., the membranes lining the roof of the mouth; pharyngeal surfaces, i.e., mucous membranes lining the pharynx; gingival surfaces, i.e., mucous membranes of the gums; and gingival sulcus, i.e., the cavity formed between the teeth and gums.

In addition, the term "oral mucosal epithelial progenitor cells" as used herein, is understood as referring to cells arising from tissue of the oral mucosa that are capable of proliferation and differentiation under controlled and/or defined conditions.

The term "serum-free" as used herein, is understood as being devoid of human or animal serum.

The term "feeder cells" as used herein, refers to cells of any one type that are co-cultured with cells of another type, to provide an environment in which the cells of the second type can grow. These feeder cells, e.g., fibroblasts, may serve as a basal layer for providing secreted factors, extracellular matrix, and cellular contacts for the maintenance of cells, e.g., pluripotent stem cells, progenitor cells, and the like, in the undifferentiated state without losing pluripotency.

As used herein, the terms "proliferate" or "proliferation" refers to an increase in the number cells in a cell culture.

According to the present disclosure, the enzymatic digestion treatment may be conducted under shaking at a speed ranging from 800 rpm to 1600 rpm. The term "shaking" as used herein, refers to a repetitive motion which may appear as a shaking motion or a generally orbital motion that is able to agitate or mix a sample by use of a shaker, e.g., orbital shaker, vortex shaker, or platform shaker. In certain embodiments, the optimal enzymatic digestion treatment is conducted under shaking at 1,200 rpm.

According to the present disclosure, the enzymatic digestion treatment may be conducted in a serum-free supplemented hormonal epithelial medium in the absence of feeder cells.

According to the present disclosure, the amniotic membrane is a denuded amniotic membrane. As used herein, the terms "denuded amniotic membrane" and "de-epithelialized amniotic membrane" can be used interchangeably, and refer to a sample of amniotic membrane where the epithelial layer has been removed.

The term "platelet lysate-containing medium" refers to a medium containing products of platelets that have been released through lysing of the platelets. In certain embodiments, the serum-free platelet lysate-containing medium includes PLTMax® platelet lysate. In an exemplary embodiment, the PLTMax® platelet lysate may be present in an amount of 5 wt % based on the total weight of the serum-free platelet lysate-containing medium that is free of feeder cells.

In certain embodiments, the serum-free platelet lysate-containing medium may further include an epithelial cell growth medium.

As used herein, the term "epithelial cell growth medium" refers to a medium used to grow epithelial cells. In certain embodiments, the epithelial cell growth medium may be a supplemented hormonal epithelial medium (SHEM).

According to the present disclosure, the supplemented hormonal epithelial medium may include a basal medium, a growth factor, and insulin.

The term "basal medium" refers to any medium that supplies a solution of salts, nutrients, amino acids and vitamins for supporting the growth of cells in culture. Examples of basal media include, but are not limited to, Dulbecco's Modified Eagle's Medium (DMEM), Minimal Essential Medium, Basal Medium Eagle, DMEM/F-12 (Nutrient Mixture F-12), DMEM/F-10 (Nutrient Mixture F-10), α-Minimal essential Medium, Glasgow's Minimal Essential Medium, KnockOut DMEM, and combinations thereof. In certain embodiments, the basal medium is DMEM/F-12 medium.

The term "growth factor" refers to any substance that is capable of stimulating cellular growth. Examples of growth factors include, but are not limited to, recombinant human epidermal growth factor, keratinocyte growth factor, hepatocyte growth factor, and combinations thereof. In certain embodiments, the growth factor is recombinant human epidermal growth factor.

In certain embodiments, the supplemented hormonal epithelial medium may further include an anti-bacterial agent and/or an anti-fungal agent.

Examples of anti-bacterial agents include, but are not limited to, penicillin, streptomycin and gentamycin. In certain embodiments, the anti-bacterial agent is gentamycin.

Examples of anti-fungal agents include, but are not limited to, amphotericin B and fluconazole. In certain embodiments, the anti-fungal agent is amphotericin B.

As used herein, the term "proliferation facilitating medium" refers to any medium that is capable of facilitating the proliferation and expansion of epithelial cell aggregates.

It should be noted that the epithelial cell growth medium as mentioned above alone may be not capable of facilitating the proliferation of cell aggregates adhered on the amniotic membrane, since the mesenchymal cells and fibroblasts that are present in the cell aggregates, as obtained by subjecting an oral mucosal tissue to an enzymatic digestion treatment with collagenase, may expand and overgrow so as to inhibit the proliferation of epithelial cell aggregates. Therefore, the cell aggregates adhered on the amniotic membrane are to be cultivated in the serum-free proliferation facilitating medium in the absence of feeder cells so as to promote the proliferation of the epithelial cell aggregates and, at the same time, suppress the proliferation of the mesenchymal cells and fibroblasts. For example, simple SHEM, DMEM, and Defined Keratinocyte Serum-Free Medium are not suitable for use as the proliferation facilitating medium. In certain embodiments, the serum-free proliferation medium free of feeder cells may replace the serum-free platelet lysate-containing medium free of feeder cells.

According to the present disclosure, the serum-free proliferation facilitating medium may include EpiLife® medium, Keratinocyte-serum free medium (SFM), Stemline® Keratinocyte Medium II, DermaLife® K Serum-Free Keratinocyte Culture Medium, and combinations thereof. In certain embodiments, the serum-free proliferation facilitating medium is EpiLife® medium.

In certain embodiments, the serum-free proliferation facilitating medium may further include a supplement. Examples of the supplement include, but are not limited to, Supplement S7, BPE-free Keratinocyte Medium Supplement, and a combination thereof. In certain embodiments, the supplement is Supplement S7.

The present disclosure will be further described in the following examples. However, it should be understood that the following examples are solely intended for the purpose of illustration and should not be construed as limiting the present disclosure in practice.

EXAMPLES

General Experimental Materials:

1. Human oral mucosal tissue and amniotic membrane (AM) were obtained in accordance with the tenets of the Declaration of Helsinki for research involving human subjects with approval from the Institutional Review Board (IRB) of Chang Gung Memorial Hospital in Taoyuan, Taiwan (IRB approval number 101-0108B and 102-5895B).
   (a) Oral mucosal tissues were obtained from 30 patients (Male:Female=26:4, mean age=53.8±13.8 years; range: 21 to 85 years) during oral surgery. Informed consent to use the tissue for study was obtained from every donor. A pathology report indicated that these were normal tissues.
   (b) The AM was obtained after elective Cesarean section and tested negative for hepatitis B and C viruses, human immunodeficiency virus, and syphilis. The obtained AM was preserved in 1:1 DMEM/glycerol at −80° C., and upon the experiment, the AM was thawed, rinsed with phosphate-buffered saline (PBS) for three times and immersed in 0.25% EDTA (2.5 g EDTA in 1000 mL PBS) at 37° C. for 1 hour, followed by gentle removal of the epithelium with a cell scraper (Corning), so as to obtain the de-epithelialized AM.
2. The following materials were purchased from Invitrogen (Carlsbad, Calif.): Dulbecco's Modified Eagle Medium (DMEM) (Cat. No. 11995065), Gibco® Dulbecco's Modified Eagle Medium: Nutrient Mixture F-12 (DMEM/F-12) (1:1) medium (Cat. No. 11330), EpiLife® medium (Cat. No. MEPI500CA), Supplement S7 (Cat. No. S0175), pH 7.4 PBS (Cat. No. 10010), and Alexa-Fluor-conjugated goat anti-mouse IgG (Cat. No. A11001).
3. Gentamycin was purchased from Standard Chem & Pharm Co. (Tainan, Taiwan).
4. Amphotericin B was purchased from Bristol-Myers Squibb (New York, N.Y.).
5. The following materials were purchased from Sigma-Aldrich (St. Louis, Mo.): dimethyl sulfoxide (DMSO) (Cat. No. D2650), methanol (Cat. No. 34860), Triton® X-100 (Cat. No. 93443), sodium fluoride (Cat. No. S7920), sodium orthovanadate (Cat. No. S5680), protease inhibitor cocktail (Cat. No. P8340), EDTA (Cat. No. E-6758), and PBS (Cat. No. P3813-10PAK).
6. PLTMax® (Cat. No. PLTM100GMP) was purchased from Mill Creek Life Sciences (Rochester, Minn.).
7. Collagenase A (Cat. No. 10103578001) was purchased from Roche Applied Science (Indianapolis, Ind.).
8. T-PER® Tissue Protein Extraction Reagent (Cat. No. 78510) was purchased from Pierce (Rockford, Ill.).
9. Recombinant human epidermal growth factor (EGF) (Cat. No. 1416-050) was purchased from CellGenix Inc. (Germany).

10. The following materials and antibodies were purchased from Santa Cruz Biotechnology (Santa Cruz, Calif.): Hoechst 33342 dye (Cat. No. SC-391054), Propidium iodide, AKT (H-136), GSK-3β (H-76), GAPDH (FL-335), $p27^{KIP1}$ (C-19) rabbit polyclonal and $p75^{NTR}$ (C20) goat polyclonal antibodies, and cytokeratin 8 (clone C51) mouse monoclonal antibody.
11. The following antibodies were purchased from Cell Signaling Technologies (Beverly, Mass.): Rabbit polyclonal antibodies against ILK, histone H3, phospho-3-catenin (S33/37), phospho-AKT (S473, clone 193H12), and phospho-GSK-3β (S9, clone 5B3).
12. The following antibodies were purchased from Abcam (La Jolla, Calif.): Cytokeratin 13 (clone 1C7), β-catenin (clone 15B8), and cyclin D1 (clone CD1.1) mouse monoclonal antibodies, and TCF4 (clone EP2033Y) rabbit monoclonal antibody.
13. BrdU mouse antibody (RPN20Ab) was purchased from Amersham, GE Healthcare (Chalfont St Giles, UK).
14. The following antibodies were purchased from Chemicon, Millipore (Billerica, Mass.): Connexin 43 (clone 4E6.2), p63 (clone 4A4) and cytokeratin 3/76 (clone AE5) mouse monoclonal antibodies.
15. Phospho-ILK (T173) rabbit polyclonal antibody was purchased from Abgent (San Diego, Calif.).
16. ΔNp63 rabbit polyclonal antibody was purchased from BioLegend (San Diego, Calif.).
17. All plastic cell culture wares were obtained from Corning Incorporated, Life Sciences (Corning, N.Y.).

Example 1. Ex Vivo Cultivation of Oral Mucosal Epithelial Cells and Oral Mucosal Epithelial Progenitor Cells The oral mucosal tissues were sterilized in 3 mL of mouthwash (Day and Night Mouthwash) for 3 minutes, washed with PBS for three times, and then cut into tiny pieces. The chopped oral mucosal tissues were then added to a 1.5 mL Eppendorf tube containing 2 mg of collagenase A in a serum-free supplementary hormonal epithelial medium (SHEM) as shown in Table 1, followed by shaking in an orbital shaker at 1200 rpm and 37° C. for 16 hours. Then, the product thus formed was centrifuged at 3500 rpm and 4° C. for 5 minutes. After removing the supernatant, the resulting cell aggregates containing oral mucosal epithelial progenitor cells and oral mucosal epithelial cells were cultivated on the de-epithelialized AM (1.5 cm×1.5 cm), which was laid on a 25-mm culture insert and air-dried overnight, with 1.5 mL of serum-free SHEM supplemented with 5% PLTMax®. Cultivation was conducted under 37° C. and 5% $CO_2$ to assist the cell aggregates in attaching on the de-epithelialized AM.

Two days later after cell adhesion, the culture medium was changed to serum-free EpiLife® medium (containing 1% Supplement S7 and 60 μM calcium), which was used for promoting cell aggregate expansion and proliferation of the epithelial cells and epithelial progenitor cells. The medium was changed every 3 days.

TABLE 1

| SHEM components | Amount |
| --- | --- |
| DMEM/F-12 medium (Gibco ®) | 500 mL |
| Recombinant human EGF (CellGro ®) | 10 ng/mL |
| Recombinant insulin (Novo Nordisk) | 10.5 μg/mL |
| Amphotericin B (Bristol-Myers Squibb) | 2.5 μg/mL |
| Gentamycin (Standard Chem & Pharm Co.) | 40 μg/mL |

For comparison with the method of the disclosure as mentioned above, a method of the prior art for ex vivo cultivation of oral mucosal epithelial cells and oral mucosal epithelial progenitor cells was performed according to Ma, D. H. et al. (2009), *Eye,* 23:1442-1450. In brief, the oral mucosal tissues were rinsed and treated with 100 μL of 1.2 IU dispase II in PBS at 37° C. for 1 hour, and then transferred to another 35-mm dish and treated with 75 μL of a 0.25% trypsin-EDTA solution at 37° C. for cell suspension. The cells were centrifuged at 950×g, and then resuspended in 1.5 mL of SHEM containing DMEM/F-12 medium (1:1, 20 mM HEPES buffer) supplemented with 5% FBS, 0.5% DMSO, 2 ng/mL recombinant human EGF, 1 mg/mL recombinant insulin, 40 μg/mL gentamycin, and 2.5 μg/mL amphotericin B. Finally, cultivation was conducted on 25-mm transwell inserts overlaid with a layer of de-epithelialized AM. The transwell inserts were co-cultured with mitomycin C-pretreated NIH/3T3 fibroblast (ATCC CRL-1658™) as feeder cells in a six-well plate under 37° C. and 5% CO2. The culture medium was changed every 3 days.

The cells formed by the method of the disclosure (hereinafter designated as Experimental Group) and those formed by the method of the prior art (hereinafter designated as Comparative Group) were collected to conduct the following experiments.

According to the preliminary observation, it was found that the cells of Experimental Group reached confluency on de-epithelialized AM after 14 days of cultivation, and the morphology thereof is more compact than that of Comparative group (data not shown), which usually took 3 weeks to reach confluency.

It has been previously shown that cytokeratin 3/76 (K3/76) is expressed in non-keratinized corneal, conjunctival, and oral mucosal epithelia, whereas cytokeratin 8 (K8) is expressed in corneal and conjunctival epithelia, but not in oral mucosal epithelia (Chen, H. C. et al. (2009), *Invest. Ophthalmol. Vis. Sci.,* 50:4660-4668). The applicants found via immunoconfocal microscopy that, similar to Comparative Group, the cells of Experimental group were also K3/76 positive and K8 negative after cultivation on de-epithelialized AM for 14 days. In addition, the expression of connexin 43 (Cx43) and cytokeratin 13 (K13) in the culture obtained by the method of the disclosure was similar to that in normal oral mucosal epithelium (Cx43+ and K13+) (data not shown), indicating that the method of the disclosure may be effective in the ex vivo cultivation of oral mucosal epithelial cells and oral mucosal epithelial progenitor cells.

Example 2. Comparison of Proliferative Potential of the Human Oral Mucosal Epithelial Cells and Oral Mucosal Epithelial Progenitor Cells Obtained by the Methods of the Disclosure and the Prior Art The proliferative potential of oral mucosal epithelial cells and oral mucosal epithelial progenitor cells cultivated ex vivo according to the methods of the present disclosure and prior art are evaluated in the following assays.

Experimental Procedures

A. Cell Colony Formation Assay:

NIH/3T3 cells were treated with 4 μg/mL mitomycin C at 37° C. for 2 hours and seeded on 35-mm dishes at $2\times10^4$ cells/$cm^2$. Subsequently, each group of oral mucosal epithelial cells and oral mucosal epithelial progenitor cells from Example 1 obtained after cultivation on de-epithelialized AM for two weeks was treated with 1.5 U dispase II for 15 min at 37° C., isolated by trypsin, and then seeded on dishes plated with mitomycin C-treated 3T3 feeder cells at a density of $5\times10^2$ cells/$cm^2$. The medium was changed every 3 days. On day 12, the cells to be evaluated were fixed in 4% paraformaldehyde in PBS for 10 minutes. The cells were then stained with 2% (wt/vol) aqueous solution of rhodamine-B (Panreac, Kuurne, Belgium) for 30 minutes and observed under a Zeiss fluorescent microscope (Oberkochen, Germany). Colony formation was determined by the number of colonies formed per dish quantified using Image J 1.29 software (NIH, Bethesda, Md.).

B. Bromodeoxyuridine (BrdU) Labeling Assay:

In order to examine cell proliferation, the BrdU labeling assay was performed in accordance with the method as set forth in Chen, H. C. et al. (2009), *Invest Ophthalmol Vis Sci,* 50:4660-4668. In brief, each group of oral mucosal epithelial cells and oral mucosal epithelial progenitor cells from Example 1 obtained after cultivation on de-epithelialized AM for one week, was fed with DMEM supplemented with 5% FBS containing 1:500 diluted BrdU labeling reagent for 1 week, and then chased for 2 weeks in BrdU-free DMEM. The resulting BrdU-labeled culture specimen was kept frozen, and then fixed with 100% pre-chilled methanol for 10 minutes. Nonspecific binding was blocked with 5% normal donkey serum (NDS) in PBS for 30 minutes. Afterward, reconstituted nuclease/anti-BrdU mouse antibody was added to the specimen, which was then incubated for 1 hour at room temperature. Subsequently, the specimen was incubated with Alexa-Fluor-conjugated goat anti-mouse IgG for another 30 minutes and then was counterstained with propidium iodide (PI). The percentage of BrdU-positive cells was calculated by dividing the number of BrdU-positive nuclei by the total number of PI-positive nuclei in five randomized fields.

C. Immunofluorescence Staining:

After two weeks of culture, the cells on de-epithelialized AM in each group were fixed in 4% formaldehyde for 15 minutes at room temperature, rinsed with PBS, permeabilized with 0.2% Triton X-100 for 15 minutes, and rinsed with PBS. After incubation with 2% bovine serum albumin for 30 minutes to block nonspecific staining, the cells were incubated with $p75^{NTR}$ and p63 primary antibodies (each at 1:100 dilution) for 24 hours at 4° C. After being washed with PBS, the cells were incubated with the corresponding Alexa-Fluor (488 or 594)-conjugated goat anti-mouse IgG antibodies for 60 minutes at room temperature. Cell nuclei were counterstained with Hoechst 33342 or PI. Sections were mounted with Gel Mount (Biomeda, Foster City, Calif.) and examined using a Zeiss fluorescent microscope (Oberkochen, Germany) or a confocal microscope (Leica, Deerfield, Ill.). Each staining was repeated for 5 times.

D. Statistics:

All data are presented as the mean±standard deviation (S.D.) calculated for each group, and at least three independent experiments were performed. The data were compared using Wilcoxon Rank-Sum Test for paired samples. SPSS 12.0 software (SPSS Inc., Chicago, Ill., USA) was used for statistical analyses. Test results are reported as two-tailed p values, where $p<0.05$* is considered statistically significant.

Figure 2:
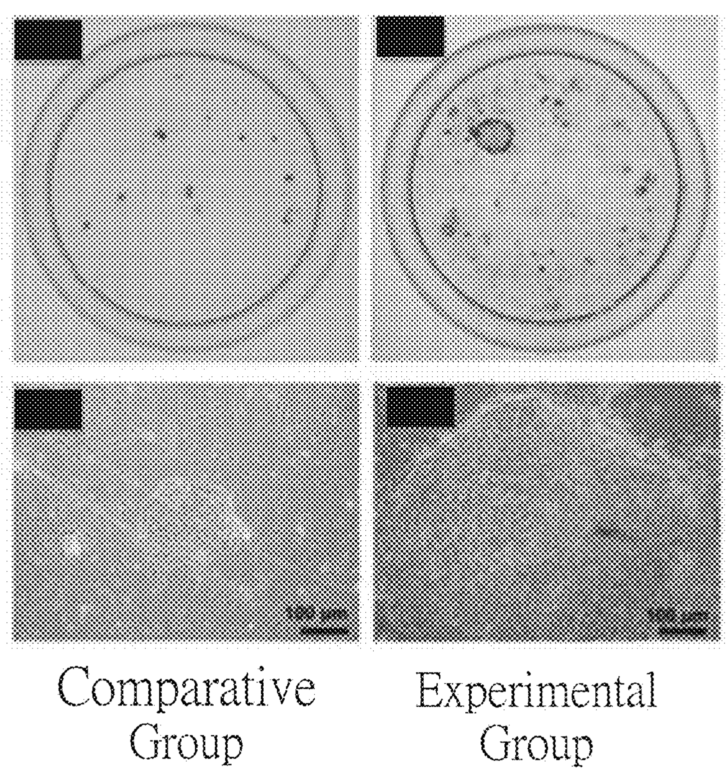
FIG. 2 illustrates the results of the colony formation assay with a depiction of the colonies formed for the cells of Experimental and Comparative Groups.

Results:

A. Cell Colony Formation Assay:

The results of the cell colony formation assay are shown in FIGS. 1-2, where it can be seen that more colonies were formed from the cells in Experimental Group as compared to Comparative Group, which suggests that the oral mucosal epithelial cells and oral mucosal epithelial progenitor cells from the method of the disclosure have a better proliferative potential. Moreover, larger colonies were generated with the method of the present disclosure, indicating that progenitor cells were better preserved with the method of the present disclosure, as seen in FIG. 2.

Figure 3:
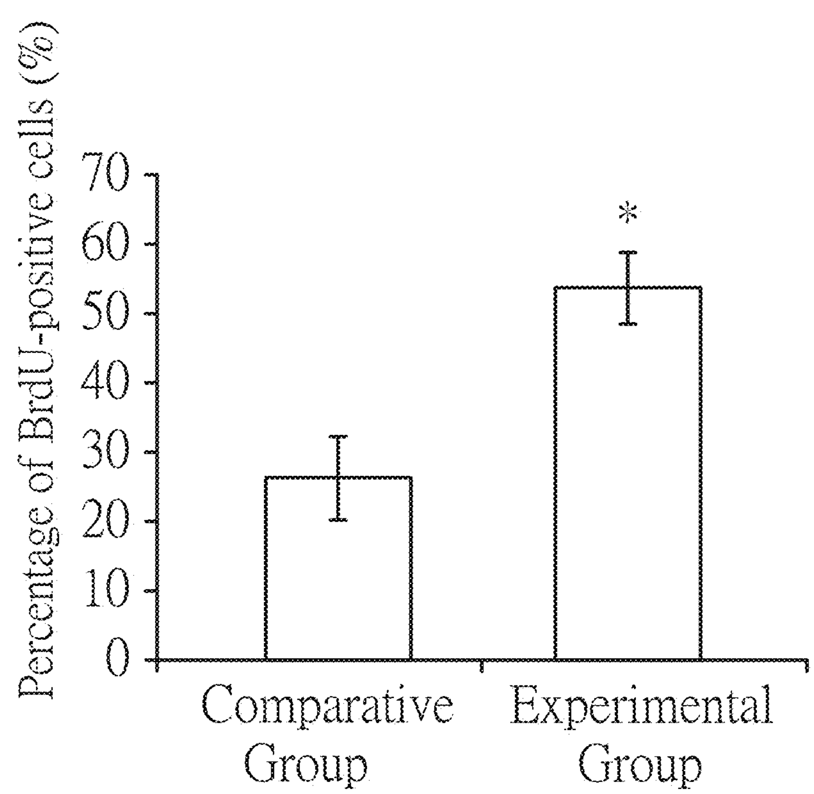
FIG. 3 illustrates the results of the BrdU labeling assay with a bar chart of the percentage of BrdU-positive cells for the cells from Experimental and Comparative Groups.

B. BrdU Labeling Assay:

FIG. 3 shows the percentages of BrdU-positive cells for the human cells obtained in Experimental and Comparative Groups. It can be seen from FIG. 3 that the percentage of BrdU-positive cells in Experimental Group was greater than that in Comparative Group.

Figure 4:
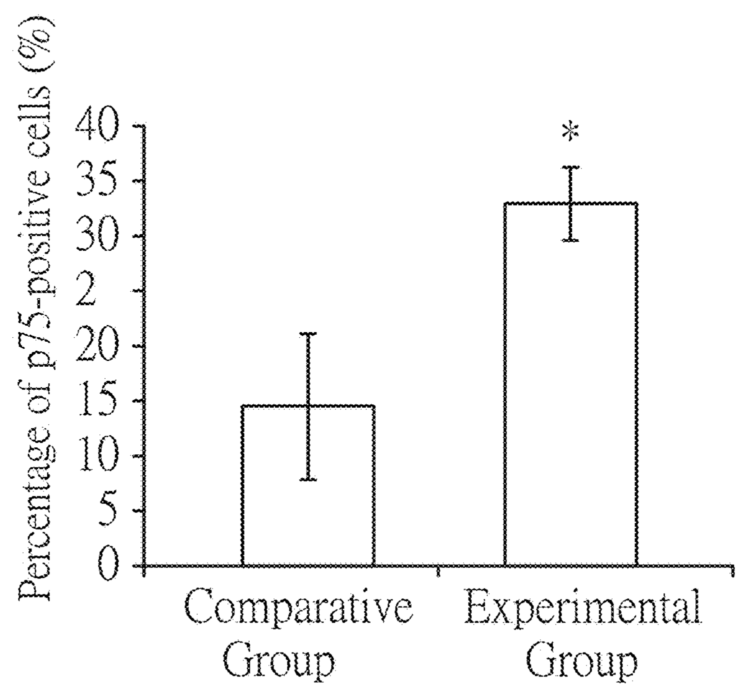
FIG. 4 illustrates the results of immunostaining with a bar chart of the percentage of $p75^{NTR}$-positive cells for the cells from Experimental and Comparative Groups.
Figure 5:
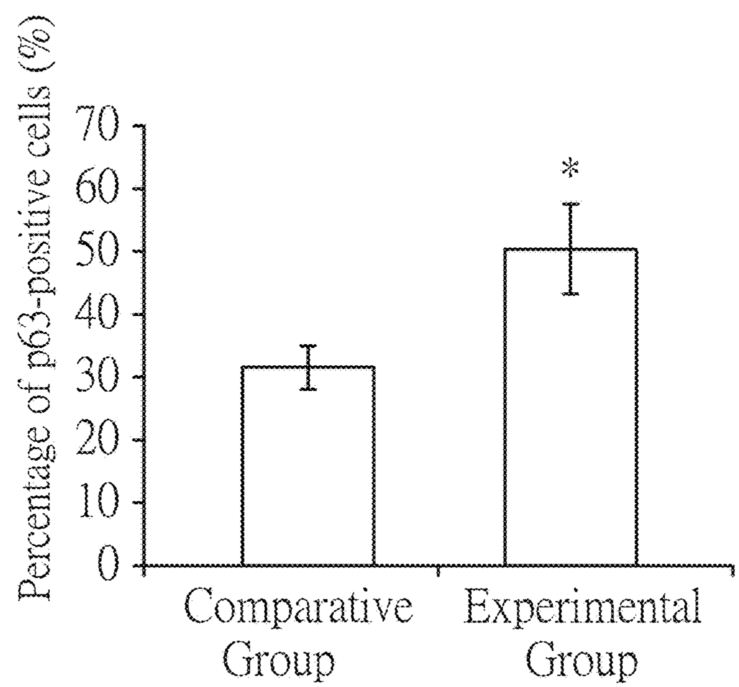
FIG. 5 illustrates the results of immunostaining with a bar chart of the percentage of p63-positive cells for the cells from Experimental and Comparative Groups.

C. Immunofluorescence Staining:

The results from immunofluorescence staining indicated that the percentages of the $p75^{NTR}$-positive cells and p63-positive cells for the human cells in Experimental Group were greater than those of Comparative Group (FIGS. 4 and 5).

From the above results of the colony formation assay, BrdU labeling assay, and p63 and $p75^{NTR}$ immunostaining, it is evident that higher proliferative potentials and more progenitor cells were preserved by the method of the present disclosure as compared to that of the prior art. It is evident that the method of the present disclosure is superior to that of the prior art in generating a human oral mucosal epithelial sheet with increased proliferative potential.

Example 3. Comparison of ILK/β-Catenin Pathway Activity in Oral Mucosal Epithelial Cells and Oral Mucosal Epithelial Progenitor Cells Cultivated Ex Vivo According to the Methods of the Disclosure and the Prior Art It is known that in epithelial cells, the β-catenin pathway can promote cell proliferation directly, through increased cyclin D1 expression, or indirectly, via suppression of the CDK inhibitor $p27^{KIP1}$ through p63 pathway activation. Therefore, in order to determine whether ILK/β-catenin pathway activation is different in the cells isolated from the methods of the present disclosure and the prior art, the applicant performed immunoblotting to analyze the phosphorylation of signal pathway-related molecules and the nuclear translocation of β-catenin.

Experimental Procedures

A. Protein Extraction and Western Blotting:

Each group of the cells on de-epithelialized AM was washed once with ice-cold PBS, and the epithelial layers were isolated by treatment with 1.5 U dispase II for 15 min at 37° C. Isolated oral mucosal epithelial cells and oral mucosal epithelial progenitor cells were suspended in 0.5 mL of T-PER® Tissue Protein Extraction Reagent supplemented with 10 mM sodium fluoride, 10 mM sodium orthovanadate, and a 1× protease inhibitor cocktail. The suspension was transferred to an Eppendorf tube on ice, sonicated to break the cells, and centrifuged in a microfuge (Labnet, Edison, N.J.) for 15 min at 4° C. at full speed. The supernatant was pooled and designated as total protein extract.

Nuclear proteins were extracted using a Nuclear Extraction kit (Affymetrix, Santa Clara, Calif.) according to the manufacturer's instructions. In brief, each group of the culture was washed twice with cold PBS, followed by addition of a 10× volume of Buffer A (supplemented with 1 mM DTT, 1× protease and phosphatase inhibitor) and incubation on ice for 10 min. The cells were released by using a sterile cell scraper, followed by pipetting to disrupt the cell clumps. The cells were then transferred to a centrifuge tube and centrifuged at 14,000×g for 3 min at 4° C. The pellets were resuspended in 150 μL of Buffer B (supplemented with 1 mM DTT, 1× protease and phosphatase inhibitor) and vortexed at full speed for 10 seconds. The resultant sample was incubated on ice for 2 hours, shaken every 20 min, and centrifuged at 14,000×g for 5 min at 4° C. The supernatant was collected and designated as the nuclear protein extract.

The concentrations of the total protein extract and nuclear protein extract in each group were determined using a Bio-Rad protein assay kit (Bio-Rad, Hercules, Calif.), and then equal amounts of proteins were resolved on acrylamide gradient gels and transferred to polyvinylidene difluoride (PVDF) membranes (Millipore). The membranes were blocked with 5% (w/v) fat-free milk in TBST (50 mM Tris-HCl, pH 7.5, 150 mM NaCl, 0.05% (v/v) Tween-20) and probed at 4° C. overnight with primary antibodies at dilutions as shown in Table 2. After washing with TBST solution 3 times, appropriate horseradish peroxidase-conjugated secondary antibodies were then added. Immunoreactive bands for each protein were visualized on X-ray film with an enhanced chemiluminescence detection system (GE Healthcare) and densitometrically quantified using Image J 1.29 software (NIH, Bethesda, Md.). The immunoreactive band density of each protein was normalized by the density of internal controls (GAPDH or histone H3), and then the relative signal intensity was expressed as Comparative Group divided by Experimental Group. Each experiment was completed with triple independent tests.

TABLE 2

| Proteins for detection | Primary antibody dilution ratio |
|---|---|
| phospho-ILK (T173) | 1:1000 |
| ILK | 1:1000 |
| phospho-AKT (S473) | 1:1000 |
| AKT | 1:500 |
| phospho-GSK 3β (S9) | 1:1000 |
| GSK 3β | 1:500 |
| (Nu) β-catenin | 1:1000 |
| phospho-β-catenin (S33/37) | 1:1000 |
| TCF4 | 1:1000 |
| ΔNp63 | 1:1000 |
| cyclinD1 | 1:1000 |
| $p27^{KIP1}$ | 1:500 |
| GAPDH | 1:10000 |

B. Statistics:

All data are presented as the mean±S.D. calculated for each group. The data were compared using Wilcoxon Rank-Sum Test for paired samples. SPSS 12.0 software (SPSS Inc., Chicago, Ill., USA) was used for statistical analyses. Test results are reported as two-tailed p values, where p<0.05* is considered statistically significant.

Results:

The relative expression of β-catenin signal pathway-related molecules between the cells of Experimental Group and Comparative Group is shown in Table 3. As shown in Table 3, regarding Experimental group, the expression of phospho-ILK (T173), phospho-AKT (S473), phospho-GSK 3β (S9) and β-catenin were significantly up-regulated, and the expression of phospho-β-catenin (S33/37) was down-regulated. Moreover, there was an increase in the expression of TCF4, Np63, and cyclin D1, whereas the expression of $p27^{KIP1}$ was decreased. These experimental data indicate increased ILK/β-catenin pathway activity and up-regulated expression of cell cycle modulators in the oral mucosal epithelial cells obtained by the method of the present disclosure.

TABLE 3

| Protein | Relative Signal Intensity (ratio ± S.D.) |
|---|---|
| phospho-ILK (T173) | 0.47 ± 0.10* |
| ILK | 1.02 ± 0.07 |
| phospho-AKT (S473) | 0.27 ± 0.16* |
| AKT | 1.07 ± 0.14 |
| phospho-GSK 3β (S9) | 0.47 ± 0.05* |
| GSK 3β | 0.91 ± 0.15 |
| (Nu) β-catenin | 0.20 ± 0.07* |
| phospho-β-catenin (S33/37) | 3.30 ± 2049* |
| TCF4 | 0.15 ± 0.04* |
| ΔNp63 | 0.34 ± 0.08* |
| cyclinD1 | 0.75 ± 0.04* |
| $p27^{KIP1}$ | 2.45 ± 0.69 |

In summary, the method of the present disclosure for the ex vivo cultivation of oral mucosal epithelial cells and oral mucosal epithelial progenitor cells (in which (i) collagenase is used to replace the conventionally used dispase II/trypsin-EDTA for digesting oral mucosal tissues, with high-speed vortexing being involved, (ii) human platelet-derived PLT-Max® is used to replace fetal bovine serum in SHEM to avoid xenogeneic infection from animal-derived products, and (iii) serum-free EpiLife® medium is used to effectively eliminate contamination by submucosal mesenchymal cells) is superior to the method of the prior art in generating human oral mucosal epithelial sheet with increased proliferative potential. Such superiority is most likely due to enhanced ILK/β-catenin pathway activity following collagenase treatment (not dispase II/trypsin treatment).

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for the ex vivo cultivation of oral mucosal epithelial progenitor cells and oral mucosal epithelial cells, comprising:

subjecting an oral mucosal tissue to an enzymatic digestion treatment with collagenase, so as to obtain cell aggregates which include oral mucosal epithelial progenitor cells and oral mucosal epithelial cells;

cultivating the cell aggregates with an amniotic membrane in a serum-free platelet lysate-containing medium in the absence of feeder cells, so that the cell aggregates are adhered onto the amniotic membrane; and cultivating the cell aggregates adhered on the amniotic membrane in a serum-free proliferation facilitating medium that is different from the serum-free platelet lysate-containing medium and is free of platelet lysate in the absence of feeder cells, so that the oral mucosal epithelial progenitor cells and the oral mucosal epithelial cells in the cell aggregates proliferate.

2. The method according to claim 1, wherein the enzymatic digestion treatment is conducted under shaking at a speed ranging from 800 rpm to 1600 rpm.

3. The method according to claim 1, wherein the enzymatic digestion treatment is conducted under shaking at 1,200 rpm.

4. The method according to claim 1, wherein the enzymatic digestion treatment is conducted in a serum-free supplemented hormonal epithelial medium in the absence of feeder cells.

5. The method according to claim 1, wherein the amniotic membrane is a denuded amniotic membrane.

6. The method according to claim 1, wherein the serum-free platelet lysate-containing medium comprises PLTMax® platelet lysate.

7. The method according to claim 6, wherein the serum-free platelet lysate-containing medium further comprises an epithelial cell growth medium.

8. The method according to claim 7, wherein the epithelial cell growth medium is a supplemented hormonal epithelial medium.

9. The method according to claim 8, wherein the supplemented hormonal epithelial medium comprises a basal medium, a growth factor, and insulin.

10. The method according to claim 9, wherein the basal medium is selected from the group consisting of Dulbecco's Modified Eagle's Medium (DMEM), Minimal Essential Medium, Basal Medium Eagle, DMEM/F-12 (Nutrient Mixture F-12), DMEM/F-10 (Nutrient Mixture F-10), α-Minimal essential Medium, Glasgow's Minimal Essential Medium, KnockOut DMEM, and combinations thereof.

11. The method according to claim 9, wherein the growth factor is selected from the group consisting of a recombinant human epidermal growth factor, keratinocyte growth factor, hepatocyte growth factor, and combinations thereof.

12. The method according to claim 1, wherein the serum-free proliferation facilitating medium is selected from the group consisting of EpiLife® medium, Keratinocyte-serum free medium (SFM), Stemline® Keratinocyte Medium II, DermaLife® K Serum-Free Keratinocyte Culture Medium, and combinations thereof.

13. The method according to claim 12, wherein the serum-free proliferation facilitating medium is EpiLife® medium.

14. The method according to claim 13, wherein the serum-free proliferation facilitating medium further comprises a supplement.

15. The method according to claim 14, wherein the supplement is selected from the group consisting of Supplement S7, BPE-free Keratinocyte Medium Supplement, and a combination thereof.

16. The method according to claim 1, wherein the serum-free proliferation facilitating medium suppresses the proliferation of mesenchymal cells and fibroblasts that are present in the cell aggregates.

17. The method according to claim 1, wherein the serum-free platelet lysate-containing medium and serum-free proliferation facilitating medium are animal-derived component-free media.

18. A method for the ex vivo cultivation of oral mucosal epithelial progenitor cells and oral mucosal epithelial cells, comprising:

subjecting an oral mucosal tissue to an enzymatic digestion treatment with collagenase, so as to obtain cell aggregates which include oral mucosal epithelial progenitor cells and oral mucosal epithelial cells;

cultivating the cell aggregates with an amniotic membrane in a serum-free platelet lysate-containing medium that includes PLTMax® platelet lysate in the absence of feeder cells, so that the cell aggregates are adhered onto the amniotic membrane; and cultivating the cell aggregates adhered on the amniotic membrane in a serum-free EpiLife® medium in the absence of feeder cells, so that the oral mucosal epithelial progenitor cells and the oral mucosal epithelial cells in the cell aggregates proliferate, and the proliferation of mesenchymal cells and fibroblasts that are present in the cell aggregates is suppressed.

* * * * *